(12) United States Patent
Bulitta et al.

(10) Patent No.: US 8,870,767 B2
(45) Date of Patent: Oct. 28, 2014

(54) ENDOCAPSULE

(75) Inventors: Clemens Bulitta, Spardorf (DE); Stefan Förtsch, Kunreuth (DE); Norbert Gläsel, Schnaittach (DE); Rainer Kuth, Höchstadt (DE); Bernhard Roas, Möhrendorf (DE); Sebastian Schmidt, Weisendorf (DE); Rainer Graumann, Höchstadt (DE); Arne Hengerer, Möhrendorf (DE); Ludwig Herbst, Eggolsheim (DE)

(73) Assignee: Siemens Aktiengesellschaft, Munich (DE)

( * ) Notice: Subject to any disclaimer, the term of this patent is extended or adjusted under 35 U.S.C. 154(b) by 591 days.

(21) Appl. No.: 12/988,422

(22) PCT Filed: Apr. 2, 2009

(86) PCT No.: PCT/EP2009/053937
§ 371 (c)(1),
(2), (4) Date: Dec. 29, 2010

(87) PCT Pub. No.: WO2009/127528
PCT Pub. Date: Oct. 22, 2009

(65) Prior Publication Data
US 2011/0092787 A1 Apr. 21, 2011

(30) Foreign Application Priority Data
Apr. 18, 2008 (DE) .......... 10 2008 019 643

(51) Int. Cl.
| | |
|---|---|
| *A61B 5/07* | (2006.01) |
| *A61B 5/145* | (2006.01) |
| *A61B 5/00* | (2006.01) |
| *A61B 1/00* | (2006.01) |
| *A61B 1/04* | (2006.01) |
| *A61B 1/05* | (2006.01) |
| *A61B 5/1459* | (2006.01) |

(52) U.S. Cl.
CPC ............. *A61B 5/073* (2013.01); *A61B 5/14542* (2013.01); *A61B 1/05* (2013.01); *A61B 5/14546* (2013.01); *A61B 5/1459* (2013.01); *A61B 5/6861* (2013.01); *A61B 1/00016* (2013.01); *A61B 5/14539* (2013.01); *A61B 5/42* (2013.01); *A61B 1/041* (2013.01); *A61B 1/00158* (2013.01)
USPC ............ 600/302; 600/309; 600/311; 600/532

(58) Field of Classification Search
CPC .. A61B 5/073; A61B 5/14532; A61B 5/1455; A61B 5/1459; A61B 5/145; A61B 5/0836
USPC .......... 600/364, 309, 312, 311, 310, 532, 302
See application file for complete search history.

(56) References Cited

U.S. PATENT DOCUMENTS

| 5,292,344 A | * | 3/1994 | Douglas .......................... 607/40 |
| 5,477,854 A | | 12/1995 | Essen-Moller |

(Continued)

FOREIGN PATENT DOCUMENTS

CN    1868396 A    11/2006

(Continued)

OTHER PUBLICATIONS

Normann, Principles of Biointrumentation, John Wiley & Sons, 1988, p. 225, 230.*

(Continued)

*Primary Examiner* — Michael Kahelin
*Assistant Examiner* — Tho Tran
(74) *Attorney, Agent, or Firm* — Schiff Hardin LLP

(57) ABSTRACT

An endocapsule has a measurement chamber therein containing a sensor that detects at least one metabolic product of a specific bacterium in a hollow organ of a human or animal gastrointestinal tract. The endocapsule is introduced into the hollow organ wherein detection of the at least one metabolic product takes place.

13 Claims, 2 Drawing Sheets

(56) References Cited

U.S. PATENT DOCUMENTS

| | | |
|---|---|---|
| 5,507,289 A | 4/1996 | Essen-Moller |
| 5,989,840 A | 11/1999 | D'Angelo et al. |
| 6,509,169 B2 | 1/2003 | Ratcliffe et al. |
| 2003/0060702 A1 | 3/2003 | Kuth et al. |
| 2004/0077093 A1* | 4/2004 | Pan .................................. 436/37 |
| 2004/0175289 A1 | 9/2004 | Takizawa et al. |
| 2006/0052667 A1 | 3/2006 | Palti et al. |
| 2007/0021654 A1 | 1/2007 | Preidel et al. |
| 2008/0188837 A1* | 8/2008 | Belsky et al. ............... 604/890.1 |
| 2008/0208077 A1 | 8/2008 | Iddan et al. |
| 2008/0302659 A1* | 12/2008 | Sheppard et al. ......... 204/403.01 |
| 2009/0177036 A1 | 7/2009 | Shimizu et al. |

FOREIGN PATENT DOCUMENTS

| | | | | |
|---|---|---|---|---|
| DE | 102005032290 | * | 1/2007 | ............... A61B 5/07 |
| DE | 102005032290 A1 | | 1/2007 | |
| EP | 643942 A1 | * | 3/1995 | ............... A61B 5/00 |
| EP | 1 695 662 A1 | | 8/2006 | |
| EP | 1 698 267 A1 | | 9/2006 | |
| JP | 07323034 A | | 12/1995 | |
| WO | 2005030114 A1 | | 9/2004 | |
| WO | WO2005113374 A2 | * | 12/2005 | ............. B65D 81/00 |
| WO | WO/2006/045011 A2 | | 4/2006 | |

OTHER PUBLICATIONS

"Possibility of Non-Invasive Diagnosis of Gastric Mucosal Precancerous Changes," Pasechnikov et al., World Journal of Gastroenterology, vol. 10, No. 21 (2004) pp. 3146-3150.

"Heliobacter Pylori Infection in Elderly Patients," Salles, La Revue de Médecine Interne, vol. 28 (2007) pp. 400-411.

* cited by examiner

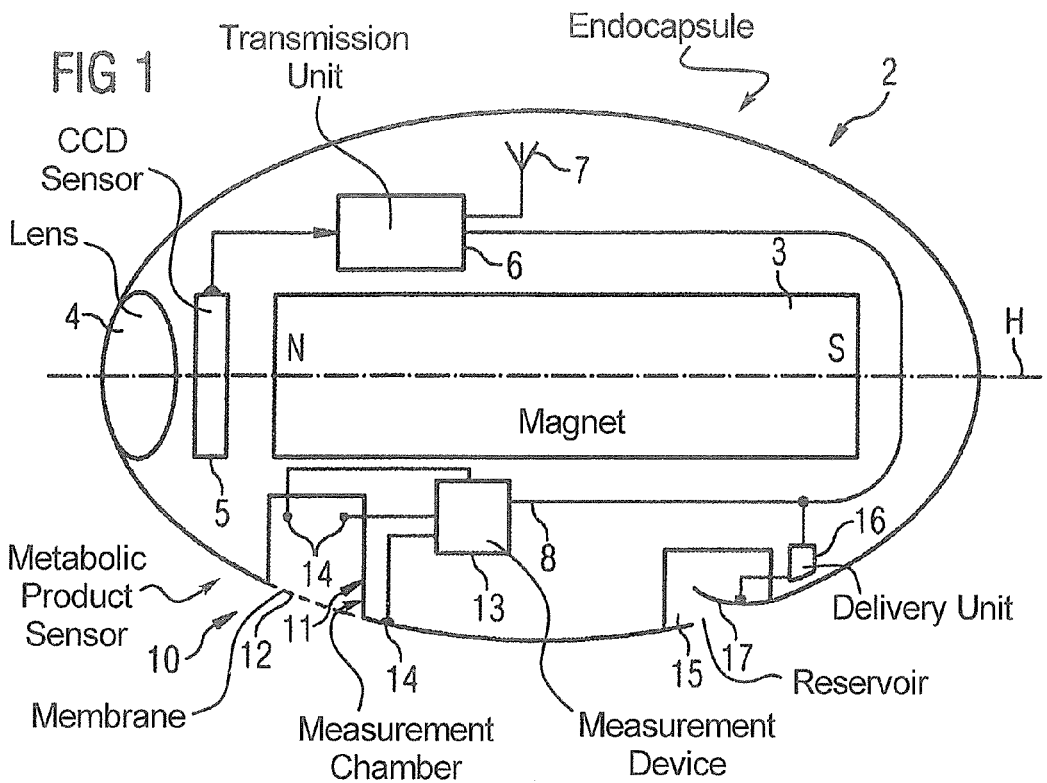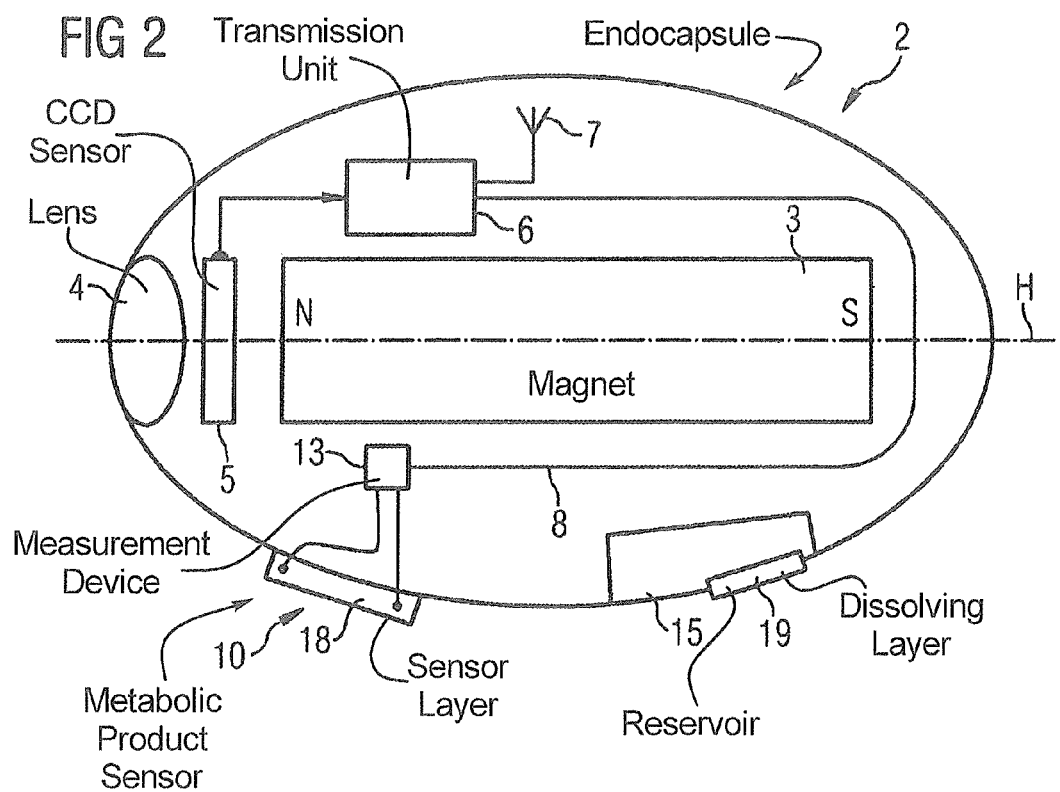

ENDOCAPSULE

BACKGROUND OF THE INVENTION

1. Field of the Invention

The invention concerns a method to detect a specific bacterium in a hollow organ of the human or animal gastrointestinal tract, and an endoscopy capsule to detect such a bacterium and its use.

2. Description of the Prior Art

A frequent cause for complaints of the upper gastrointestinal tract is a bacterial attack of its organs. For example, an attack by *Helicobacter pylori* has been held responsible for a large range of stomach illnesses that are accompanied by an intensified secretion of stomach acid. Type B gastritis, approximately 75% of gastric ulcers and nearly all duodenal ulcers fall into this category, for example. The examination of the hollow organs of the gastrointestinal tract for colonization by bacteria—in particular for colonization with *Helicobacter pylori*—is therefore an important component of the diagnosis of stomach illnesses. d by For example, *Helicobacter pylori* is detected a breath test in which urea marked with C-13 is administered to the patient. The C-13-marked $CO_2$ that arises upon splitting urea into ammonia and $CO_2$ is detected in the exhaled air. Other methods to detect *Helicobacter pylori* are based on typical blood values of, for example pepsinogen or gastrin. However, such methods are complicated and less reliable.

An additional possibility to examine the stomach for a colonization with *Helicobacter pylori* is known as gastroscopy ("stomach endoscopy"). During such an examination the gastroenterologist takes a biopsy of the stomach mucosa in order to examine this sample at a later point in time for an infection with *Helicobacter pylori*. A known examination method for the tissue sample (biopsy specimen) is the *Helicobacter* urease test (HU test, abbreviated as HUT), for example. The biopsy specimen is placed in a testing medium (measurement solution) that contains a culture medium for this bacterium that consists of urea and an indicator (litmus). If the *Helicobacter pylori* bacterium is contained in the sample, the bacterium splits the urea ($CO(NH_2)_2$) via urease into ammonia ($NH_3$) and carbon dioxide ($CO_2$). The ammonia then colors the indicator red. The test result is detectable after a few minutes. The initial color change from yellow to red, however, cannot be clearly established under disadvantageous conditions.

Gastroscopy has a low patient acceptance and is unsuitable for conducting screening examinations.

One alternative to the above-described examination of the upper gastrointestinal tract that is implemented endoscopically (stomach endoscopy) is the use of an endoscopy capsule, which is also called an endocapsule or capsule endoscope and is known from DE 101 42 253 C1 and the corresponding US 2003/0060702 A1, for example. Such an endocapsule is a capsule that can be swallowed, the capsule communicating wirelessly with a transmission station outside of the patient's body. The endocapsule moreover, can be navigable in a magnetic gradient field. Such a capsule can be outfitted with sensors that allow it to measure or detect temperature, electrical conductivity, pH value or chemical substances inside a hollow organ, for example. Such an endocapsule can likewise be suitable for targeted administration of medicine.

A method is described in WO 2004/039233 A2. in which the pH value is determined via an in vivo measurement. Ammonium ($NH_4^+$) is detected in the stomach via this pH measurement, whereby a conclusion of the presence of *Helicobacter pylori* should be possible. However, this test for *Helicobacter pylori* is not reliable since an acid medium (pH value between 1.5 and 2) does not necessarily have to be present in the stomach. Deviations from an acid medium can occur due to the taking of medication, diet and/or health status. Deviations from the ideal state (pH value between 1.5 and 2) lead to a massive adulteration of the measurement result, such that the measured pH value allows no conclusion of the ammonia concentration (and therefore of a presence of *Helicobacter pylori*).

SUMMARY OF THE INVENTION

An object of the present invention is to provide an endocapsule and a method with such an endocapsule to detect a specific bacterium in a hollow organ of the human or animal gastrointestinal tract.

In the method according to the invention to detect a specific bacterium in a hollow organ of the human or animal gastrointestinal tract, the bacterium is detected using at least one of its metabolic products with an endocapsule containing a sensor for said metabolic product, the endocapsule being introduced into the hollow organ. A bacterium can be identified with great certainty using its metabolic products. With the use of the endocapsule the metabolic products are detected directly at the location of their creation (thus in situ). Although such an endocapsule is typically swallowed, it is completely inert within the body. For this reason the method according to the invention has a high patient acceptance. The swallowing of an endocapsule is very patient-friendly in comparison to the detection methods known from the prior art, for example endoscopic examinations including a biopsy. Moreover, since the metabolic products are measured directly at the location of their creation inside the hollow organ of the gastrointestinal tract, the detection of the bacterium ensues with high precision and measurement certainty. The method according to the invention uses the endocapsule as the sole item of analysis equipment; advantageously, no additional resources—for example additional laboratory or analysis devices—are required to detect the specific bacterium.

According to a first embodiment, an initial substance that can be resorbed by the specific bacterium is supplied to the hollow organ. In other words, an initial substance is supplied to the hollow organ that is selected such that it can be metabolized by the bacterium whose detection is sought. At least one metabolic product of the bacterium which is created from the initial substance is now detected. The targeted administration of an initial substance increases the production of the bacterium with regard to the metabolic product whose detection is sought. The concentration of the metabolic product in the hollow organ rises; the detection is simpler and more precise due to the increased level.

The presence of a specific bacterium can be concluded with high probability from the combination of initial substance, end product and bacterium. For example, if the detection of a specific bacterium is sought, a suitable initial substance (for which it is known that it will be metabolized by the bacterium) can be supplied to the hollow organ. In this case an increased level of the associated metabolic product should be detectable. Given a negatively conducted detection, an initial substance can be supplied to the hollow organ for which it is known that it is not metabolized by the bacterium. Nevertheless, if a metabolic product which is to be associated with this initial substance can be detected, this could indicate an error in the direct detection. For example, the initial substance can be administered in the form of a tablet or capsule which disintegrates in the hollow organ (for example the stomach).

In each case the detection certainty of the method can be increased by the targeted administration of an initial substance.

According to a further embodiment, the concentration of the metabolic product is measured at least once before introducing the initial substance into the hollow organ and at least once after introducing the initial substance into the hollow organ. Such a procedure allows a relative measurement that, in the simplest case, is determined by the difference of the values before and after introducing the initial substance. Such a relative measurement allows the detection of a specific bacterium using a metabolic product which also occurs in the absence of the bacterium in the hollow organ. For example, if the initial concentration of a specific metabolic product in the hollow organ is initially measured, after administration of the initial substance—and waiting a possibly necessary duration of effect—a markedly increased value of the metabolic product relative to the initial concentration represents a very strong indicator of the presence of the specific bacterium.

In an embodiment, the measurements of the concentration of the metabolic product are related to that point in time at which the initial substance is introduced into the hollow organ. By this point in time being accounted for (known) in the measurement of the concentration of the metabolic product, it is possible to take into account specific time constants for the bacterium whose detection is sought. For example, it is thus possible that a bacterium has produced a sufficient amount of metabolic product only after a certain time period. A measurement which would be implemented too early after the introduction of the initial substance into the hollow organ would be less significant since the concentration of the metabolic product relative to the base value would only have risen too slightly. The time correlation of the concentration measurement with the point in time of the administration of the initial substance allows such a time response of the bacterium to be taken into account. The detection certainty can be increased.

According to a further embodiment, the time curve of the concentration of at least one metabolic product is determined using a plurality of chronologically successive measurements. A time-dependent concentration curve of the metabolic product allows the time response of the productivity of the bacterium to be studied in relation to the observed metabolic product. Such a time-dependent curve allows a differentiated assessment of the reaction of the special bacterium to the administered initial substance.

According to another embodiment, the specific bacterium is *Helicobacter pylori*, to which urea is administered as an initial substance via introduction into the hollow organ. Carbon dioxide ($CO_2$) is detected as a metabolic product. *Helicobacter pylori* has been held responsible for a plurality of different disease patterns of the hollow organs of the gastrointestinal tract. Its detection therefore represents an important intermediate step in the diagnosis of corresponding illnesses. *Helicobacter pylori* breaks down urea ($CO(NH_2)_2$) into hydrogen carbonate ($HCO_3^-$) and ammonia ($NH_3$). In the aqueous environment of the gastrointestinal tract, the hydrogen carbonate decays into carbon dioxide and water. The fluid present in the hollow organ—for example the gastric juices—are accordingly enriched with $CO_2$. The increased $CO_2$ content of the gastric juices can be determined using a difference measurement before and after administration of the urea. *Helicobacter pylori* is detected using an increased $CO_2$ concentration of the gastric juices.

According to a further embodiment, *Helicobacter pylori* which is offered urea ($CO(NH_2)_2$) from an initial substance via introduction into the hollow organ is detected using ammonia ($NH_3$) as a metabolic product. *Helicobacter pylori* generates ammonia in order to protect itself from the acid environment of the gastrointestinal tract, in particular the high hydrochloric acid concentration in the stomach. Locally present ammonia leads to a neutralization of the stomach mucosa in the region of the colonization with *Helicobacter pylori*. Since ammonia does not occur (or occurs only in very slight concentration) in a hollow organ of the gastrointestinal tract (for example the stomach) under normal circumstances, its detection is sufficient as a very strong indication of the presence of *Helicobacter pylori*.

A combination of ammonia measurement with, for example a measurement of $CO_2$ content serves to increase the detection certainty but is not absolutely necessary. The same is likewise true with a combination of the measurement of the $NH_3$ or $CO_2$ content in connection with an additional measurement method, for example a blood test or breath test.

According to a further embodiment, the initial substance is introduced into the hollow organ by the endocapsule. The initial substance can thus advantageously be offered directly to the bacterium that are possibly present in the hollow organ. A corresponding reaction to the bacterium can be measured using the more or less immediately rising level of the reaction products.

According to another embodiment, the initial substance is introduced into a conspicuous sub-region of the hollow organ. This conspicuous sub-region has previously been identified using an optical examination, for example with the aid of a camera located on board the endocapsule. The identification of conspicuous regions can ensue extracorporeally by purely optical examination or using dyes such as Congo red or methylene blue. Depending on the type of chemoendoscopy, those regions of the hollow organ that are colonized by the specific bacterium (in particular *Helicobacter pylori*) can be dyed. Given that the initial substance is specifically introduced into the presumably affected regions of the hollow organ, a local detection of the affliction can be directed there.

The endocapsule according to the invention, which can be introduced into a hollow organ of the human or animal gastrointestinal tract, has a sensor that is designed to respond to a metabolic product of a specific bacterium.

Significant advantages of the endocapsule according to the invention have been cited in connection with the method according to the invention.

According to a first embodiment, the sensor of the endocapsule comprises a sensor field in connection with its environment, which sensor field has a sensor layer which experiences a measurable property change upon contact with the bacterium or its metabolic products. Depending on the field of use of the endocapsule, this can advantageously be provided with the matching sensor layer which respectively reacts sensitively to those bacteria or metabolic products whose detection is sought.

According to a further embodiment, the sensor has a resistance measurement device to measure the ohmic resistance of the sensor layer or a densiometer arrangement to measure the optical density of the sensor layer. The measurement of the ohmic resistance or, respectively, the optical density can technically be controlled well and therefore can be implemented simply and precisely. Moreover, a wide spectrum of property changes of the sensor layer is detected using these two physical parameters.

According to an embodiment, the sensor layer is composed of silver chloride. Silver chloride dissolves in ammonia but is resistant to stomach acid. Ammonia is a strong indication of the presence of *Helicobacter pylori*. For this reason a silver chloride layer as a sensor layer is well suited for the detection of *Helicobacter pylori*.

According to a further embodiment, the sensor has a measurement chamber that is closed off from the environment of the endocapsule by a membrane that is preferably permeable to the metabolic product. A membrane with such properties is typically designated as "semipermeable". Such a design of the endocapsule has the effect that the metabolic product accumulates in the measurement chamber; its concentration here is thus significantly higher than in the environment of the endocapsule. Even low concentrations of the metabolic product can be detected easily and with certainty with the aid of an intensification effect achieved in this manner.

According to another embodiment, a particularly simple possibility for detection is given in that the sensor of the endocapsule comprises a voltage measurement device with which the potential difference between the outside of the endocapsule and the inside of the measurement chamber can be measured.

According to a further embodiment, the sensor comprises a pH measurement device to measure the pH in the measurement chamber. Potential difference measurements and pH value measurements can technically be reliably done and allow a simple and certain detection of the metabolic product.

According to one embodiment, the sensor of the endocapsule has a membrane that is preferably permeable to ammonia. The presence of ammonia is a strong indication of a colonization with *Helicobacter pylori*. Such an endocapsule is therefore in particular suitable for the detection of this bacterium.

According to a further embodiment, the sensor of the endocapsule has a carbon dioxide sensor. An increased carbon dioxide concentration in a hollow organ of the gastrointestinal tract is likewise a strong indication of the presence of *Helicobacter pylori*.

According to another embodiment, the endocapsule has a reservoir is closed off from the outside of the endocapsule by a layer that is soluble in gastric juices. The reservoir can be sealed particularly simply in the indicated manner.

According to a further embodiment, the endocapsule has a controllable delivery device with which the initial substance can be released from the reservoir or, respectively, be dispensed to the environment of the endocapsule. Such a delivery device can be a valve, for example. A device is likewise conceivable with which a barrier—for example a film—with which the reservoir is closed off from the outside area is removed or destroyed.

BRIEF DESCRIPTION OF THE DRAWINGS

FIG. 1 schematically illustrates a first embodiment of an endocapsule according to the invention, in longitudinal section.

FIG. 2 schematically illustrates a second embodiment of an endocapsule according to the invention, in longitudinal section.

DESCRIPTION OF THE PREFERRED EMBODIMENTS

Figure 3:
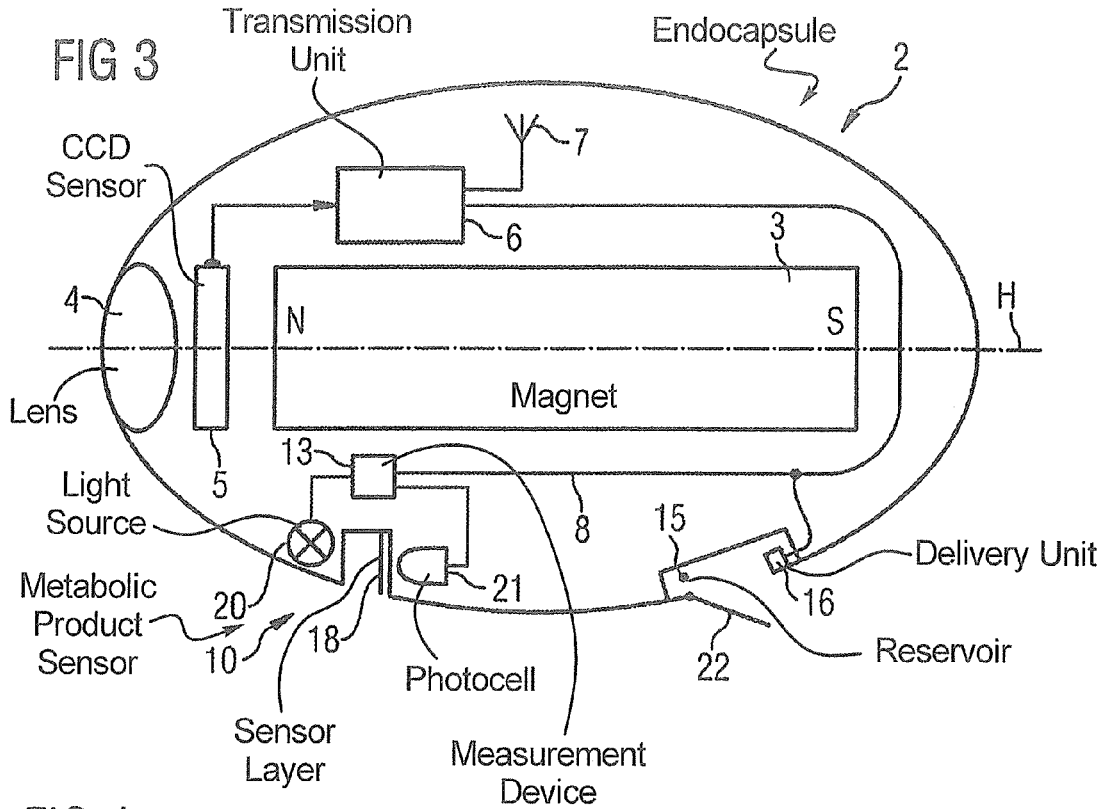
FIG. 3 schematically illustrates a third embodiment of an endocapsule according to the invention, in longitudinal section.

An endocapsule 2 shown in FIG. 1 has a housing that is essentially elipsoid-shaped relative to the primary axis H. Located inside the endocapsule 2 is a bar magnet 3 that is colinear with the primary axis H, which bar magnet 3 enables the navigation (produced by magnetic forces) of the endocapsule 2 in a magnetic gradient field. A lens 4 is mounted flush in the housing in the front region of the endocapsule 2. A CCD sensor 5 to acquire image data is arranged on the inside of the lens 4. The acquired image data are sent to a transmission station (remote from the endocapsule 2) with the use of a transmission unit 6 which has both the function of a transmitter and the function of a receiver. The transmission unit 6 is connected with an antenna 7 for wireless data transmission. The transmission station is discussed in detail below.

The endocapsule 2 shown in FIG. 1 serves to detect *Helicobacter pylori* in the human stomach. This bacterium generates ammonia as a typical metabolic product. The colonization of the stomach with *Helicobacter pylori* can therefore be detected in that the ammonia content of the gastric juices or the ammonia content in the mucus of the inner stomach wall (stomach mucosa) is measured.

The endocapsule 2 has a metabolic product sensor 10 that has a measurement chamber 11 arranged inside the endocapsule 2. This is closed off from the outside space of the endocapsule 2 with a membrane 12 that is preferably permeable to ammonia. Ammonia can consequently accumulate in the inner area of the measurement chamber 11 when the outside of the membrane 12 is in contact with a fluid containing ammonia. The detection of the ammonia in the measurement chamber 11 ensues alternatively via measurement of the potential difference between the outer area of the endocapsule 2 and the inner space of the measurement chamber 11 or via measurement of the pH value inside the measurement chamber 11. The endoscopy capsule 2 has a suitable measurement device 13 to conduct such measurements. This is a voltage measurement device (potentiometer) or a pH measurement device, as needed. The measurement device 13 is connected with electrodes 14 that are arranged inside the measurement chamber 11 or on the outside of the endocapsule 2 and allow corresponding measurements.

The measurement data acquired with the aid of the measurement device 13 are sent to the transmission unit 6 via a data line 8. The measurement data are transmitted to the transmission station located at a distance from the endocapsule 2 with the aid of the transmission unit 6.

The endocapsule 2 also has a reservoir 15 located in its internal space, which reservoir 15 serves to accommodate urea as an initial substance for *Helicobacter pylori*. The reservoir 15 can be opened with the use of a delivery unit 16 so that the urea present in it is dispensed into the environment of the endocapsule 2. A control unit that is connected with the transmission unit 6 via the data line 8 serves as a delivery unit. The control unit can be remotely controlled from the transmission station, such that the urea dispensing by the endocapsule 2 can be specifically influenced. The reservoir 15 is sealed with a bi-metal 17 which is charged with current with the aid of the delivery unit 16 to open the reservoir 15.

The endocapsule 2 shown in FIG. 1 can optionally comprise a $CO_2$ sensor (not shown in detail), for example a Severinghaus electrode. With this it is possible to measure the $CO_2$ concentration of the gastric juices.

FIG. 2 shows a second exemplary embodiment of an endocapsule 2. This possesses a sensor layer 18 made of silver chloride arranged in a sensor field, which sensor layer 18 is located in a lower region as part of the sensor 10. Given contact with urea, the silver chloride layer—which is otherwise insoluble in the acid gastric juices—begins to dissolve. The cross section of the sensor layer 18 that is reduced as a consequence of the dissolving process leads to a change of its ohmic resistance, which is measured with the measurement device 13. The measurement values are transferred via the data line 8 to the transmission unit 6 and from there are transmitted to the transmission station located at a distance from the endocapsule 2.

The reservoir 15 arranged inside the endocapsule 2 is sealed with a layer 19. This layer 19 dissolves slowly in the acid gastric juices, such that ultimately the initial substance that is present in the internal space 15 is dispensed from the endocapsule 2.

FIG. 3 shows a third exemplary embodiment of an endocapsule 2. This embodiment includes a densiometer arrangement as a sensor 10 with whose help the optical properties of the sensor layer 18 are measured. The sensor layer 18 (likewise made of silver chloride) is located in a measurement area that is accessible from the outside of the endocapsule 2. Its optical transmittance/density is measured in that it is exposed by a light source 20 and the optical transmission is measured with the aid of a photocell 21. This measurement ensues with the measurement device 13 which sends the measurement data via the data line 8 to the transmission unit 6 for transmission to the remote transmission station. The reservoir 15 (likewise arranged in the internal space of the endocapsule 2) is closed off from the external space of the endocapsule 2 with a flap 22. The flap 22 can be opened by remote control with the aid of the delivery unit 16.

Figure 4:
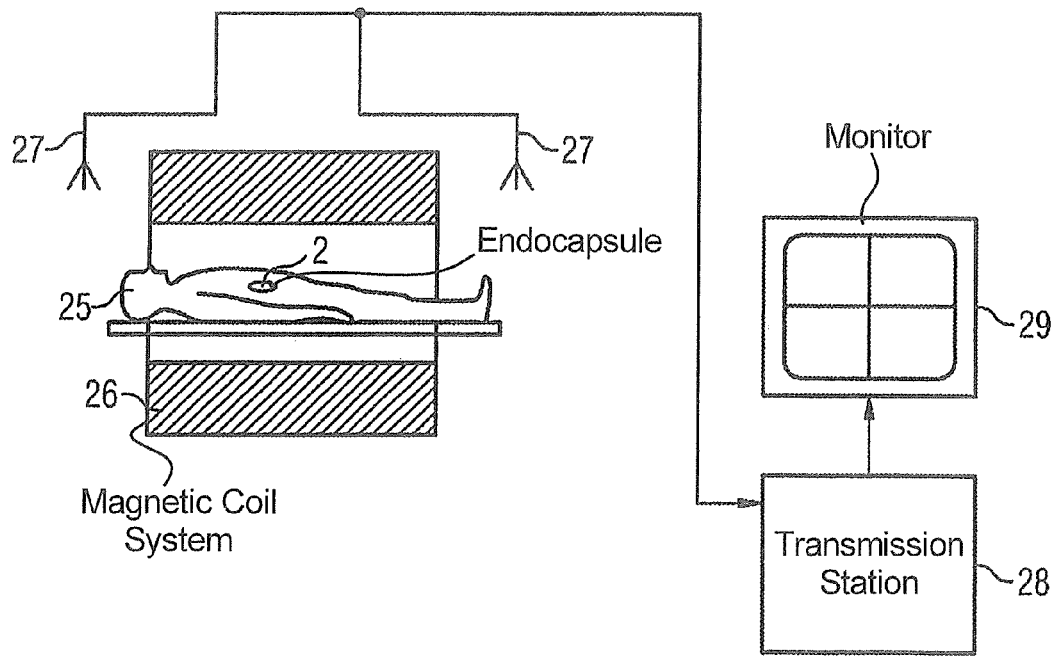
FIG. 4 schematically illustrates a medical work space in which the method according to the invention can be implemented.

FIG. 4 shows a medical work space. A patient 25 is located in a magnetic coil system 26 that is suitable for magnetic capsule endoscopy. The endocapsule 2 that can be magnetically navigated with the aid of the magnetic coil system 26 is located in the stomach of the patient 25. The data sent from the transmission unit 6 of the endocapsule 2 are received with the aid of antennas 27 and relayed to the transmission station 28. The information received by the endocapsule 2—for example image information, concentration values of ammonia ($NH_3$) or carbon dioxide ($CO_2$) etc.—are visualized on a monitor 29.

Although modifications and changes may be suggested by those skilled in the art, it is the intention of the inventors to embody within the patent warranted heron all changes and modifications as reasonably and properly come within the scope of their contribution to the art.

The invention claimed is:

1. A method to detect a specific bacterium in a hollow organ of the gastrointestinal tract of a subject, comprising the steps of:
   storing an initial substance in a reservoir of an endocapsule, said reservoir having an opening that communicates an interior of said reservoir with an exterior environment of said endocapsule, said initial substance being resorbable by said bacterium;
   maintaining said opening covered with an electronically operable closure element to confine said initial substance to said interior of said reservoir;
   providing said endocapsule with a measurement chamber having an interior in which a sensor is located that detects at least one metabolic product associated with said bacterium;
   closing off said interior of said measurement chamber from said exterior environment of said endocapsule except for a membrane that is semi-permeable for said at least one metabolic product;
   introducing said endocapsule into said gastrointestinal tract of the subject;
   from a control unit in said endocapsule, electronically operating said closure element to uncover said opening and introduce said initial substance into the hollow organ of the subject, by releasing said initial substance from the reservoir, and thereby causing said initial substance to be resorbed by the bacterium, when the bacterium is present in the hollow organ, so as to generate said at least one metabolic product from interaction of the initial substance with the bacterium when said bacterium is present in the hollow organ; and
   only after a defined time following uncovering of said opening, that allows intensified accumulation of said at least one metabolic product in said measurement chamber via said membrane while said endocapsule is located in the gastrointestinal tract of the subject, initiating operating said sensor from said control unit to detect said intensified accumulation of said metabolic product in said measurement chamber, and using the detected at least one metabolic product as an indication of the presence of said bacterium in the hollow organ, and emitting an extracorporeally detectable data signal from said control unit that represents said indication.

2. A method as claimed in claim 1 comprising measuring a concentration of said at least one metabolic product at least once before introducing said initial substance into the hollow organ from the reservoir, and measuring the concentration of the metabolic product at least once after introducing said initial substance into the hollow organ from the reservoir.

3. A method as claimed in claim 2 comprising making each of said measurements before and after introducing the initial substance into the hollow organ from the reservoir at respective times having a defined relationship to a time at which the initial substance is introduced into the hollow organ from the reservoir.

4. A method as claimed in claim 2 comprising making a plurality of chronologically successive measurements of said concentration, and determining a time curve of said concentration of said metabolic product from said plurality of chronologically successive measurements.

5. A method as claimed in claim 1 comprising introducing urea as said initial substance and detecting a presence of Helicobacter pylori when carbon dioxide is detected as said at least one metabolic product.

6. A method as claimed in claim 1 comprising introducing urea as said initial substance and detecting a presence of Helicobacter pylori when ammonia is detected as said at least one metabolic product.

7. A method as claimed in claim 1 comprising generating a visual image of an inner wall of the hollow organ in which the endocapsule is located, and introducing said initial substance from the reservoir into a visually identifiable sub-region of the hollow organ from the endocapsule by examination of said visual image.

8. A method as claimed in claim 1 comprising additionally detecting said at least one metabolic product from the group consisting of a blood test and breath test.

9. An endocapsule comprising:
   an endocapsule body configured for introduction into a hollow organ of the gastrointestinal tract of a subject;
   said endocapsule body having a reservoir therein containing an initial substance, said reservoir having an opening that communicates an interior of said reservoir with an exterior environment of said endocapsule, said initial substance being resorbable by a bacterium;

an electronically operable closure element that covers said opening to confine said initial substance to said interior of said reservoir;

said endocapsule body having a measurement chamber therein having an interior in which a sensor is located that detects at least one metabolic product associated with said bacterium;

a membrane that is semi-permeable for said at least one metabolic product, said membrane closing off said interior of said measurement chamber from said exterior environment of said endocapsule body except for said membrane;

a control unit in said endocapsule body configured to electronically operate said closure element to uncover said opening and introduce said initial substance into the hollow organ of the subject, by releasing said initial substance from the reservoir, and thereby causing said initial substance to be resorbed by the bacterium, when the bacterium is present in the hollow organ, so as to generate said at least one metabolic product from interaction of the initial substance with the bacterium when said bacterium is present in the hollow organ; and said control unit being configured, only after a defined time following uncovering of said opening, that allows intensified accumulation of said at least one metabolic product in said measurement chamber via said membrane while said endocapsule is located in the gastrointestinal tract of the subject, to initiate operation of said sensor from said control unit to detect said intensified accumulation of said metabolic product in said measurement chamber, and to use the detected at least one metabolic product as an indication of the presence of said bacterium in the hollow organ, and to emit an extracorporeally detectable data signal from said control unit that represents said indication.

10. An endocapsule as claimed in claim 9 wherein said sensor is a voltage measurement device that measures a potential difference between an exterior of said endocapsule and said interior of said measurement chamber.

11. An endocapsule as claimed in claim 9 wherein said sensor is a pH sensor that measures pH in said measurement chamber.

12. An endocapsule as claimed in claim 9 wherein said sensor detects ammonia and wherein said membrane is semi-permeable to ammonia.

13. An endocapsule as claimed in claim 9 wherein said sensor detects carbon dioxide and wherein said membrane is semi-permeable to carbon dioxide.

* * * * *